United States Patent [19]

Weber et al.

[11] 4,221,793
[45] Sep. 9, 1980

[54] N,N'-DISUBSTITUTED PIPERAZINE DERIVATIVE

[75] Inventors: Rolf-Ortwin Weber, Wiesbaden-Naurod; Klaus Perrey, Langenfeld; Wolfrad von Rechenberg, Ludwigshafen-Oggersheim, all of Fed. Rep. of Germany

[73] Assignee: Hoechst Aktiengesellschaft, Frankfurt, Fed. Rep. of Germany

[21] Appl. No.: 972,068

[22] Filed: Dec. 21, 1978

[30] Foreign Application Priority Data

Dec. 23, 1977 [DE] Fed. Rep. of Germany ....... 2757532

[51] Int. Cl.$^2$ .................. A61K 31/495; C07D 405/06
[52] U.S. Cl. ................................. 424/250; 544/376; 260/346.22
[58] Field of Search ......................... 544/376; 424/250

[56] References Cited

U.S. PATENT DOCUMENTS 4,115,569   9/1978   Weber et al. ...................... 544/376

Primary Examiner—Paul M. Coughlan, Jr.
Attorney, Agent, or Firm—Quaintance, Murphy & Richardson

[57] ABSTRACT

A compound of the formula

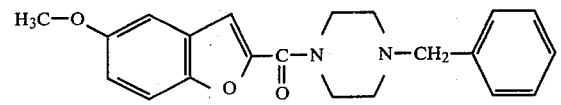

or its acid addition salt with a physiologically compatible acid, a process for its preparation by a reaction selected from the group consisting of
(a) reacting N-benzyl-piperazine and 5-methoxycumarilic acid
  (a1) at an elevated temperature in the absence of a condensation agent,
  (a2) at a temperature of at least 15° C. in the presence of a condensation agent;
(b) reacting N-benzyl-piperazine with an activated derivative of 5-methoxy-cumarilic acid;
(c) N-(5-methoxycumaroyl)-piperazine with a benzyl compound selected from the group consisting of benzyl halide, benzylalkyl sulfonate and benzylaryl sulfonate and a pharmaceutical composition containing said compounds.

2 Claims, No Drawings

N,N'-DISUBSTITUTED PIPERAZINE DERIVATIVE

N,N'-Disubstituted cyclic diamines and acid addition salts thereof, as well as their pharmacological properties, have been described. Although these substances have proved to be therapeutically successful, it is desired to extend the available cyclic diamines by introducing selected substituents in a planned manner into the 5-position of a benzofuran system, the compounds obtained having a certain structural relationship to the neuro-transmitter, serotonin.

According to one aspect of the invention there is provided a compound of formula

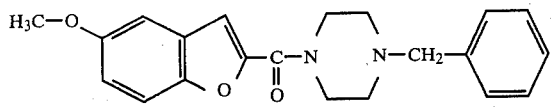

and physiologically acceptable acid addition salts thereof.

The compound according to the invention may be prepared by the following processes, which processes form further aspects of the invention:

(a) reacting N-benzyl-piperazine with 5-methoxycumarilic acid either
 (a1) at an elevated temperature in the absence of a condensation agent, or
 (a2) at a temperature of at least 15° C. in the presence of one or more condensation agents;

(b) reacting N-benzyl-piperazine with a reactive derivative of 5-methoxycumarilic acid, such as an anhydride, halide, ester, amide or azide thereof; or (c) reacting N-(5-methoxycumaroyl)-piperazine with a benzyl halide, benzyl alkylsulphonate or benzyl arylsulphonate.

In process a1) according to the invention amide formation is obtained thermally with elimination of water by heating the two reagents, preferably in the absence of a solvent, to a temperature of from 130° to 280° C., preferably to over 150° C. This embodiment is an especially simple and rapid process with which a practically complete reaction may be achieved. In this process the reaction mixture is desirably maintained in the above-specified temperature range until elimination of water (which is advantageously distilled continuously from the reaction mixture) is complete. Removal of water formed in the reaction may be accelerated by passing a gas which is inert under the reaction conditions, such as nitrogen or a rare gas, through the reaction mixture.

If the free acid and the free amine are reacted according to process (a2) of the invention in the presence of substances assisting the formation of a carboxylic acid amide group, work is conveniently carried out, for example, at a temperature of from 20° to 150° C., preferably at temperatures up to the boiling point of the reaction mixture. A solvent, e.g. tetrahydrofuran or the solvents mentioned below are preferably present for this process. Dehydrating agents assisting the formation of a carboxylic acid amide group include, for example, carbodiimides (e.g. 1,3-dicyclohexylcarbodiimide, 1-cyclohexyl-3-[2-(4-morpholinyl)-ethyl]carbodiimide, 1-(3-dimethylaminopropyl)-3-ethylcarbodiimide hydrochloride, 1,3-di-p-tolylcarbodiimide and 1,3-diisopropyl-carbodiimide); and dialkyl cyanamides with from 1 to 4 carbon atoms in the alkyl radical, e.g. diethyl cyanamide. These dehydrating agents, as well as the diamine and the acid component are conveniently employed in equimolar quantities. However, the molar ratios thereof may occasionally exceed or fall below this optimum ratio.

Process (b) employs a reactive derivative of the carboxylic acid. Especially preferred compounds for this purpose are, for example, acid halides(and advantageously the chloride or bromide); esters with alcohols preferably having 1 to 4 carbon atoms or phenols optionally substituted with nitro groups or chlorine atoms; a symmetrical anhydride or mixed anhydride thereof (preferably of alkyl, phenylalkyl or phenylcarboxylic acid hemi-esters, wherein the alkyl groups may each contain 1 to 4 carbon atoms); or, amides thereof, especially of azoles and azines, such as imidazole, triazole, benzotriazole or s-triazine, which may be readily prepared by reacting equimolar quantities of carboxylic acid and N,N'-carbonyl-diimidazole, -triazole, -benzotriazole or -s-triazine at room temperature in tetrahydrofuran, chloroform or a similar solvent which is inert under the reaction conditions (see for example H. A. STAAB, Angew. Chem. 74, 407 (1962)).

When a carboxylic acid halide is used and similarly when N-(5-methoxycumaroyl)-piperazine is reacted with an alkylating agent according to process (c), work is advantageously carried out in the presence of an alkali metal carbonate, such as sodium or potassium carbonate, a tertiary amine such as pyridine, picoline or triethylamine or with molar, excess of the cyclic diamine. Generally these processes are effected in an inert solvent such as benzene, toluene, xylene and at a temperature of 15° to 50° C., optionally up to the boiling point of the reaction mixture. A preferred embodiment of this process consists in effecting the reaction in dimethylformamide. In this case, the final product serves simultaneously as an acid binding agent and is produced as a hydrohalide. The salts produced primarily in this embodiment may be optionally converted into other acid addition salts in a way known per se, eg by double decomposition.

An especial advantage of effecting the reaction in dimethylformamide is its considerable purification activity. For this reason, also, this process is to be preferred. The product may be isolated in a conventional way, e.g. by precipitation. Furthermore, the reaction of process b), advantageously the reaction of N-benzyl piperazine with a 5-methoxycumarilic acid halide, is especially easy to carry out in dimethylformamide from a technical point of view as it proceeds without undesired side reactions and consequently gives a high yield. The molar ratio of the reaction components is preferably selected at 1:1; however, other molar ratios, also e.g. 3:1 to 1:3, and conveniently 1.5:1 to 1:1.5, are possible. The solvent employed may be reused and the reaction components are readily available.

Examples of acids which may be used for converting the compound of formula I according to the invention obtained as a base into physiologically compatible acid addition salts include hydrohalic acids, especially hydrochloric acid, sulphuric, phosphoric, p-toluenesulphonic, methanesulphonic acid, and cyclohexylamidosulphonic acid.

The substance according to the invention is characterised by interesting pharmacological properties. Thus, in the tetrabenazine catalepsy test it has shown a substantially stronger effect than the commercially available comparison substance, imipramine, and also has a considerably lower toxicity, so that it has a substantially higher therapeutic index. The compound according to the invention is therefore suitable as a psychotherapeutic medicament which is largely free of the undesirable side-effects which often limit the therapeutic applicability of other medicaments. The compound according to the invention especially has not shown in therapeutically relevant doses any cardiotoxic, central nervous system stimulation, or sedation activities or any influence on the vegetative nervous system. Consequently, it differs advantageously from the comparable known substances having an anti-depressant activity.

The stability of the crystalline compound and of its acid addition salts enables drug preparations to be prepared, e.g. for oral, parenteral and rectal administration. In another aspect, the invention therefore provides pharmaceutical compositions comprising the substance according to the invention in association with a pharmaceutical carrier or excipient. The compositions are especially suitable as psychopharmaceuticals. The dosage of the compound of the invention may desirably be for example 10 to 400, preferably 50 to 200 mg per day. When in the form of dosage units the compositions may contain e.g. 10 to 150, preferably 25 to 100 mg of the active ingredient.

These compositions may be made according to conventional practice by admixing suitable and compatible adjuvants such as starch, lactose, cellulose derivatives, stearic acid or salts thereof, solvents, dissolving intermediaries, suppository masses, chlorides, phosphates and carbonates, e.g. sodium bicarbonate; and may be in the form of, for example, powders, tablets, coated tablets, capsules, suppositories, solutions or suspensions. However, the administration of microcapsules without any additive is also possible.

The following examples serve to illustrate the preparation of the compound according to the invention and also acid addition salts thereof:

Example 1

(a) 5-Methoxycumarilic acid chloride 576 g of 5-methoxycumarilic acid (3 mol) are mixed well with 625. 5 g of phosphorus pentachloride (3 mol) and 3 ml of phosphorus oxytrichloride are added to the mixture. During the exothermic reaction the mixture liquefies with a large release of hydrogen chloride. The phosphorus oxytrichloride is subsequently distilled off under the reduced pressure obtained with a water-jet pump and the residue is fractionated twice. For easier handling, the hot distillate is poured as a melt into thin plates.

Yield: 593.7 g (94.0% of theory), boiling point: 175° C. (20 mb), melting point: 80°–82° C.

(b) N-(5-Methoxybenzofuran-2-ylcarbonyl)-N'-benzylpiperazine hydrochloride

A mixture of 352 g of N-benzyl-piperazine (2 mol) and 2 liters of dimethylformamide is mixed with a solution of 421 g of 5-methoxycumarilic acid chloride (2 mol) in 600 ml of dimethylformamide. After an exothermic reaction a crystalline deposit is obtained which dissolves again upon heating. The reaction mixture is refluxed for one hour and after cooling to approximately 110° C. is poured into 5 liters of acetone with vigorous stirring. The crystal mass formed is cooled to room temperature. For complete precipitation of the hydrochloride, the suspension is made strongly acid with 37% aqueous hydrochloric acid (approximately 100 ml) while stirring. The solid product is filtered off and washed with acetone until the filtrate runs off colourless. The compound obtained in a 95% crude yield is subsequently recrystallised in succession from dimethylformamide and water.

Yield: 660 g (85% of theory), melting range: 238°–246° C. with decomposition; base: 79° C. (diethyl ether).

EXAMPLE 2

A solution of 35.2 g of N-benzyl-piperazine (0.2 mol) in 250 ml of xylene is mixed with 30.4 g of finely powdered anydrous potassium carbonate (0.22 mol). With vigorous stirring, 42.1 g of 5-methoxycumarilic acid chloride (0.2 mol), dissolved in 200 ml of xylene, are added thereto over 5 minutes at room temperature. The reaction mixture is refluxed for 3 hours with stirring. After cooling to room temperature the solution is filtered from the solid product and the filtrate is evaporated under reduced pressure. The evaporation residue is dissolved in 300 ml of methanol and mixed with ethereal hydrochloric acid. The deposit obtained is washed with acetone and ether. The yield of the above-mentioned hydrochloride is 63.8 g corresponding to 82.5%. For further purification, the substance is recrystallised from dimethylformamide and subsequently from water.

EXAMPLE 3

A solution of 1053 g (5 mol) of freshly distilled 5-methoxycumarilic acid chloride in 2 liters of toluene is added to a solution of 1760 g of N-benzyl-piperazine (10 mol) in 10 liters of toluene, in a cast with vigorous stirring so that a homogenous mixture is obtained, if possible, before precipitation of the deposit. A thick deposit is formed rapidly which causes the reaction mixture to solidify. Shaking or stirring is carried out frequently over a period of approximately 2 hours. After cooling to room temperature the solid product is removed by suction filtration and washed with toluene and subsequently with acetone. The solid consists of N-benzyl-piperazine hydrochloride from which the base may be recovered. The filtrate (toluene-acetone solution) is mixed with ethereal hydrochloric acid. The solid product obtained is recrystallised first from dimethylformamide and then from water.

Yield: 1702 g (88% of theory). The yield may occasionally also be up to 92%.

EXAMPLE 4

A solution of 21 g of 5-methoxycumarilic acid chloride (0.1 mol) in 180 ml of pyridine is mixed with a solution of 17.6 g of N-benzyl-piperazine (0.1 mol) in 70 ml of pyridine. The mixture is refluxed for 30 minutes. It is cooled, the solvent is evaporated off and the residue is boiled with 200 ml of water. After cooling the base is dissolved in methylene chloride, the methylene chloride solution is washed twice with water and dried over sodium sulphate and the methylene chloride is removed under reduced pressure. The base thus obtained may be converted into the hydrochloride by conventional methods.

Yield: over 80% of theory.

EXAMPLE 5

22 g of ethyl 5-methoxycumarilate (0.1 mol) and 17.6 g of N-benzyl-piperazine (0.1 mol) are heated to boiling in 100 ml of xylene under reflux until thin-layer chromatography tests show complete reaction. The reaction mixture is acidified with ethereal hydrochloric acid and the solid product is removed and recrystallised in succession from dimethylformamide and water. The desired 5-methoxy-cumarilic acid piperazide derivative is obtained in the form of a colourless crystalline substance. Melting point: 238°–246° C. (decomposition).

EXAMPLE 6

28.8 g of 5-methoxycumarilic acid (0.15 mol) and 26.4 g of N-benzyl-piperazine (0.15 mol) are heated in 300 ml of tetrahydrofuran until a clear solution is obtained. After cooling to room temperature, a solution of 30.9 g of dicyclohexylcarbodiimide (0.15 mol) is added and the mixture is left to stand overnight at room temperature and then filtered from the precipitated dicyclohexyl urea. The solution is evaporated and the residue is recrystallised several times from ether.

The corresponding base of melting point 79° C. is thereby obtained and may be converted into the hydrochloride by conventional methods.

EXAMPLE 7

2.6 g of 5-methoxycumarilic acid piperazide (0.01 mol) are suspended in 10 ml of xylene and mixed with a solution of 0.6 g of benzyl chloride (0.005 mol) in 5 ml of xylene. The mixture is maintained at boiling temperature for 1 hour and then cooled, the resulting methoxycumarilic acid piperazide hydrochloride is separated and the filtrate is mixed with ethereal hydrochloric acid. The deposit obtained is isolated and recrystallised first from dimethylformamide and then from water, Yield: approximately 96.5%.

The isolated 5-methoxycumarilic acid piperazide hydrochloride according to the invention may be used for other preparations after the base has been released with sodium bicarbonate solution.

EXAMPLE 8

A mixture of 57.5 g of 5-methoxycumarilic acid (0.3 mol) and 52.8 g of N-benzyl-piperazine (0.3 mol) is heated to 250° C., the components all being melted from approximately 170° C. Separation of water begins at approximately 210° C. The reaction mixture is maintained at 250° C. until the desired quantity of water (0.3 mol) has been separated. The residue is dissolved in ethanol and mixed with ethereal hydrochloric acid and the solid product obtained is recrystallised several times from dimethylformamide and finally from water. Yield: 65%.

PHARMACOLOGICAL TESTS

The pharmacological activity of the substance according to the invention was investigated in the tetrabenazine catalepsy test and in the reserpine antagonism test at the mouse.

TETRABENAZINE CATALEPSY TEST

Mice in groups of 10 animals each were given 15 mg/kg of tetrabenazine i.p. 30 minutes after administration of the test substance. The onset of a cataleptic condition is assessed on a 2-step round cork on to which the animals are placed so that they touch the bottom step with their head and forepaws and the upper step with their hind paws. Such a position is corrected immediately by a normal animal. For assessment, the reaction of the animals is observed every 60 seconds. The inhibition of catatonia is calculated in percentage values in relation to a control group.

The results obtained with this arrangement as well as the $LD_{50}$ values from acute toxicity tests on mice are set out in Tables 1 and 2, and are shown in comparison with the known substance, imipramine.

Table 1:

| | | Tetrabenazine catalepsy test on mice, Influence on the duration of catalepsy | | | |
|---|---|---|---|---|---|
| Substance | Dose in mg/kg p.o. | Change of duration of catalepsy relative to control in % (min. post appl.) | | | n* |
| | | 20 | 60 | 120 | |
| According to the invention | 10 | −62 ± 11 | −50 ± 5 | −62 ± 13 | 40 |
| | 20 | −62 ± 26 | −69 ± 3 | −57 ± 12 | 40 |
| | 40 | −81 ± 11 | −76 ± 15 | −82 ± 17 | 30 |
| Imipramine (comparison) | 25 | −19 ± 19 | −38 ± 12 | −25 ± 17 | 30 |
| | 50 | −23 ± 6 | −48 ± 9 | −34 ± 6 | 20 |

*n = no. of animals

Table 2:

| | Toxicity in mice | | |
|---|---|---|---|
| Substance | n (= number of animals) | $LD_{50}$ (mice in mg/kg) | |
| | | i.p. | p.o |
| According to the invention | 5 | 548 | >4000 |
| Imipramine | 5 | 130 | 380 |

The results given in Table 1 show that the compound according to the invention exhibits, in the tetrabenazine catalepsy test, a substantially stronger effect than the comparison substance.

It has also been determined that in the reserpine antagonism test on mice, the substance according to the invention is substantially equal in activity compared with the comparison substance.

As indicated in Table 2, the preparation according to the invention is, in addition, on oral administration more than ten times more compatible than the comparison preparation, so that a substantially higher therapeutic index is obtained.

The compound according to the invention has also been examined for its influenece on coronary circulation and on the heart mechanogram in isolated guinea-pig hearts according to the method of Langendorff (Langendorff, O., Pfluegers Arch. 61 (1895), 219) as well as for its spasmolytic activity on isolated guinea-pig intestines according to the method of Magnus (Magnus, R., Pflugers Arch. 102 (1904), 123). In this latter case, the spasmolytic activity was determined in relation to 0.2 μg/ml of histamine and 100 μg/ml of barium chloride. The $ED_{50}$ values of the substance according to the invention and the values of the commercial product imipramine used for comparison are compiled in Table 3.

Table 3:

| | | Activity on the isolated guinea-pig heart | | Spasmolytic activity as ED$_{50}$ in μg/ml relative to | |
|---|---|---|---|---|---|
| Substance | Dose in μg | Change in coronary circulation in % | Influence on contraction level | Histamine | BaCl$_2$ |
| According to the invention | 50 | +39 | 0 | 5–10 | 5–10 |
| Imipramine (Comparison) | 10 | +19/ −18 | −25% | 0.001 | 0.1–1 |
| | 20 | +28/ −29 | −25% | | |
| | 30 | +84/ −22 | −50% | | |

Activity on isolated guinea-pig hearts and on isolated guinea-pig intestines

As shown by Table 3, the compound according to the invention does not influence the contraction level of the isolated heart and causes a dilation of the coronary vessels. In contrast thereto, although the comparison substance causes initially a brief increase in circulation, this then changes to a constriction and consequently results in heart damage which is shown by the reduction of the heart contraction.

The spasmolytic activity of the compound according to the invention is only small. It may be concluded therefrom that the peripheral vegetative nervous system is influenced only slightly, if at all, by administration of the compound. The substance may not therefore lead to undesirable side-effects such as anti-cholinergic and anti-histamine effects.

It is not intended that the examples given herein should be construed to limit the invention thereto, but rather they are submitted to illustrate some of the specific embodiments of the invention. Resort may be had to various modifications and variations of the present invention without departing from the spirit of the discovery or the scope of the appended claims.

What we claim is:

1. A compound of the formula

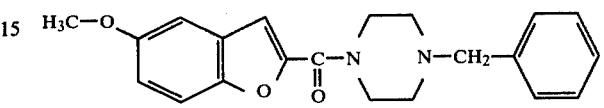

or its acid addition salt with a physiologically compatible acid.

2. A composition containing as an essential ingredient a therapeutically active amount of a compound as claimed in claim 1 wherein the therapeutically active amount of the compound as claimed in claim 1 is in the form of a dosage unit in an amount between 10 and 100 mg.

* * * * *